US011751853B2

(12) United States Patent
Taniguchi

(10) Patent No.: US 11,751,853 B2
(45) Date of Patent: Sep. 12, 2023

(54) ULTRASOUND DIAGNOSTIC APPARATUS AND ULTRASOUND IMAGE GENERATING METHOD

(71) Applicant: Konica Minolta, Inc., Tokyo (JP)

(72) Inventor: Tetsuya Taniguchi, Tokyo (JP)

(73) Assignee: KONICA MINOLTA, INC., Tokyo (JP)

( * ) Notice: Subject to any disclaimer, the term of this patent is extended or adjusted under 35 U.S.C. 154(b) by 848 days.

(21) Appl. No.: 16/669,259

(22) Filed: Oct. 30, 2019

(65) Prior Publication Data
US 2020/0163653 A1 May 28, 2020

(30) Foreign Application Priority Data

Nov. 22, 2018 (JP) .................................. 2018-219264

(51) Int. Cl.
*A61B 8/00* (2006.01)
*B06B 1/02* (2006.01)
(Continued)

(52) U.S. Cl.
CPC .................. *A61B 8/54* (2013.01); *A61B 8/14* (2013.01); *A61B 8/4488* (2013.01);
(Continued)

(58) Field of Classification Search
CPC ........... A61B 8/54; A61B 8/14; A61B 8/4488; A61B 8/5207; A61B 8/5269;
(Continued)

(56) References Cited

U.S. PATENT DOCUMENTS

2005/0124882 A1* 6/2005 Ladabaum .......... G01S 15/8925
600/437
2006/0058671 A1* 3/2006 Vitek ...................... A61N 7/02
600/447
(Continued)

FOREIGN PATENT DOCUMENTS

JP 2000300554 A 10/2000
JP 2002301068 A 10/2002
(Continued)

OTHER PUBLICATIONS

JPO, Office Action for the related Japanese Application No. 2018-219264, dated Jul. 12, 2022, with English translation.

*Primary Examiner* — Isam A Alsomiri
*Assistant Examiner* — Joseph C Fritchman
(74) *Attorney, Agent, or Firm* — LUCAS & MERCANTI, LLP

(57) ABSTRACT

An ultrasound diagnostic apparatus of the present invention includes: a transmitter that generates and outputs a plurality of drive signals to a transducer of an ultrasound probe, the drive signals causing the transducer to transmit a plurality of transmission ultrasound waves that have different waveforms in a temporally shifted manner, the drive signals being compensated for asymmetry of the transmission sound pressure waveforms of the plurality of transmission ultrasound waves transmitted from the transducer; and a hardware processor configured to extract a harmonic component according to a plurality of reception signals, and generating an ultrasound image based on the extracted harmonic component.

12 Claims, 12 Drawing Sheets

CANCELLATION DRIVE WAVEFORM

(51) Int. Cl.
  *A61B 8/14*    (2006.01)
  *G01S 7/52*    (2006.01)
  *G01S 15/89*   (2006.01)
  *A61B 8/08*    (2006.01)

(52) U.S. Cl.
  CPC .......... *A61B 8/5207* (2013.01); *A61B 8/5269* (2013.01); *B06B 1/0215* (2013.01); *B06B 1/0292* (2013.01); *G01S 7/5202* (2013.01); *G01S 7/52038* (2013.01); *G01S 7/52077* (2013.01); *G01S 15/8915* (2013.01); *G01S 15/8963* (2013.01); *B06B 2201/51* (2013.01); *B06B 2201/55* (2013.01); *B06B 2201/76* (2013.01)

(58) Field of Classification Search
  CPC . B06B 1/0215; B06B 1/0292; B06B 2201/51; B06B 2201/55; B06B 2201/76; G01S 7/5202; G01S 7/52038; G01S 7/52077; G01S 15/8915; G01S 15/8963
  See application file for complete search history.

(56) References Cited

U.S. PATENT DOCUMENTS

| | | | |
|---|---|---|---|
| 2006/0173342 A1* | 8/2006 | Panda | B06B 1/0292 600/447 |
| 2013/0331699 A1* | 12/2013 | Ishihara | A61B 8/14 600/443 |
| 2016/0120516 A1* | 5/2016 | Imagawa | A61B 8/4488 600/459 |

FOREIGN PATENT DOCUMENTS

| | | |
|---|---|---|
| JP | 2003310609 A | 11/2003 |
| JP | 2013-165882 A | 8/2013 |
| JP | 2015-006234 A | 1/2015 |

* cited by examiner

| 1 | 2 | 3 | 4 | 5 | 6 | 7 | 8 | 9 | 10 | 11 |
|---|---|---|---|---|---|---|---|---|---|---|
| W1 | W1a | W1 | W1b | W1 | W1a | W1 | W1b | W1 | W1a | W1 |

FIG. 4

FIRST DRIVE SIGNAL

SECOND DRIVE SIGNAL

TRANSMISSION SOUND
PRESSURE WAVEFORM

ADDED TRANSMISSION
SOUND PRESSURE
WAVEFORM

CANCELLATION DRIVE
WAVEFORM

APPROXIMATE DRIVE
WAVEFORM

FIRST PULSE
CONTROL SIGNAL

SECOND PULSE
CONTROL SIGNAL

FIRST DRIVE SIGNAL AND
SECOND DRIVE SIGNAL

ADDED DRIVE SIGNAL

ULTRASOUND DIAGNOSTIC APPARATUS AND ULTRASOUND IMAGE GENERATING METHOD

CROSS REFERENCE TO RELATED APPLICATIONS

The entire disclosure of Japanese Patent Application No. 2018-219264 filed on Nov. 22, 2018, is incorporated herein by reference in its entirety.

BACKGROUND

Technological Field

The present invention relates to an ultrasound diagnostic apparatus and an ultrasound image generating method that use ultrasound waves.

Description of Related Art

An ultrasound diagnostic apparatus is useful for repeated inspections because it can obtain heart beats and fetal movements in a real-time representation by a simple operation, that is, simply placing an ultrasound probe on a body surface, and is highly safe.

Such an ultrasound diagnostic apparatus may in some cases be used with an imaging method for imaging a harmonic component (for example, frequencies 2f0, 3f0, and the like) of a reflected ultrasound wave (reception signal) with respect to a fundamental wave component (frequency f0) of a transmitted ultrasound wave. Such an imaging method is called tissue harmonic imaging, and is known for providing images with good contrast.

The above-described harmonic component results mainly from nonlinear distortion that occurs when an ultrasound wave propagates through a subject. To be specific, when an ultrasound wave is emitted into a living body, the ultrasound signal is distorted during propagation through tissue due to the non-linear response of the tissue, and harmonic components increase. Consequently, the reflected signal from the tissue includes harmonics having a frequency component that is an integral multiple of the fundamental wave f0. Examples of harmonics include one referred to as second harmonic that includes the frequency component 2f0 that is twice the fundamental wave f0, and one referred to as third harmonic that includes the frequency component 3f0 that is three times the same.

In order to obtain a clear image by tissue harmonic imaging, it is important to remove the fundamental component from the reception signal and extract only the harmonic components. For example, the pulse inversion method is known as a method for extracting only the harmonic components from the reception signal. In the pulse inversion method, first and second transmission waveforms having opposite polarities are transmitted at time intervals, and each reception signal is phased and added to cancel the fundamental wave component, thereby emphasizing the second harmonic component. For example, Japanese Patent Application Laid-Open Nos. 2000-300554, 2002-301068, and 2003-310609 disclose techniques for achieving tissue harmonic imaging by the pulse inversion method.

SUMMARY

However, in the medical field, an ultrasound diagnostic apparatus that is compact, inexpensive, and easy to handle may be required. In a compact and inexpensive ultrasound diagnostic apparatus, the expensive transmission drive apparatus used in PTLs 1 to 3 cannot be adopted, which results in a compromise in terms of image quality such as resolution and penetration.

In view of such circumstances, an object of the present invention is to provide an ultrasound diagnostic apparatus and an ultrasound image generating method that can provide clear ultrasound images with an inexpensive configuration.

To achieve at least one of the abovementioned objects, according to an aspect of the present invention, an ultrasound diagnostic apparatus reflecting one aspect of the present invention comprises: a transmitter that generates and outputs a plurality of drive signals to a transducer of an ultrasound probe, the drive signals causing the transducer to transmit a plurality of transmission ultrasound waves that have different waveforms in a temporally shifted manner, the drive signals being compensated for asymmetry of the transmission sound pressure waveforms of the plurality of transmission ultrasound waves transmitted from the transducer; and a hardware processor which acquires, from the ultrasound probe, a reception signal based on a reflected ultrasound wave that is the transmission ultrasound wave reflected in a subject, extracts a harmonic component according to a plurality of reception signals corresponding to the plurality of transmission ultrasound waves, and generates an ultrasound image based on the extracted harmonic component.

BRIEF DESCRIPTION OF DRAWINGS

The advantages and features provided by one or more embodiments of the invention will become more fully understood from the detailed description given hereinbelow and the appended drawings which are given by way of illustration only, and thus are not intended as a definition of the limits of the present invention:

FIG. 4 is a diagram showing an example of drive signal array data;

DETAILED DESCRIPTION OF EMBODIMENTS

Hereinafter, one or more embodiments of the present invention will be described with reference to the drawings. However, the scope of the invention is not limited to the disclosed embodiments.

First Embodiment

The first embodiment of the present invention will be described below.

[Outline of Each Component]

Figure 1:
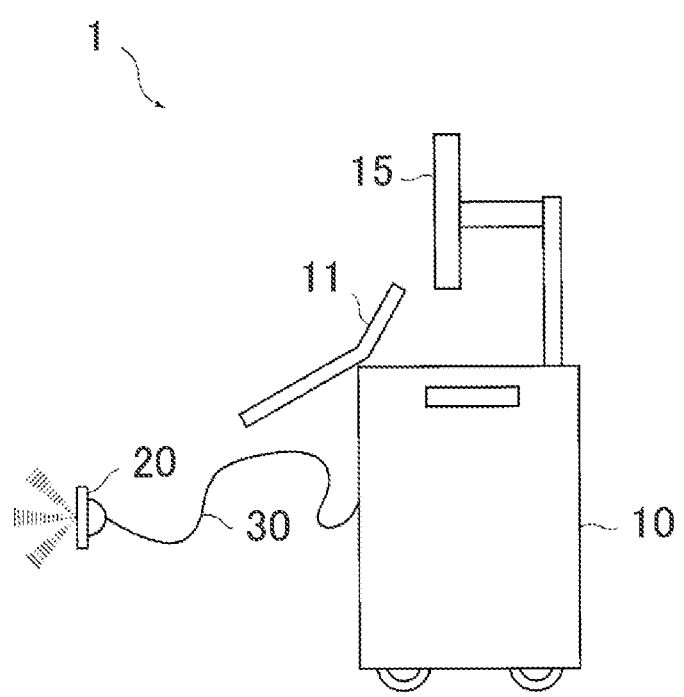
FIG. 1 is a diagram illustrating an external configuration of an ultrasound diagnostic apparatus.
Figure 2:
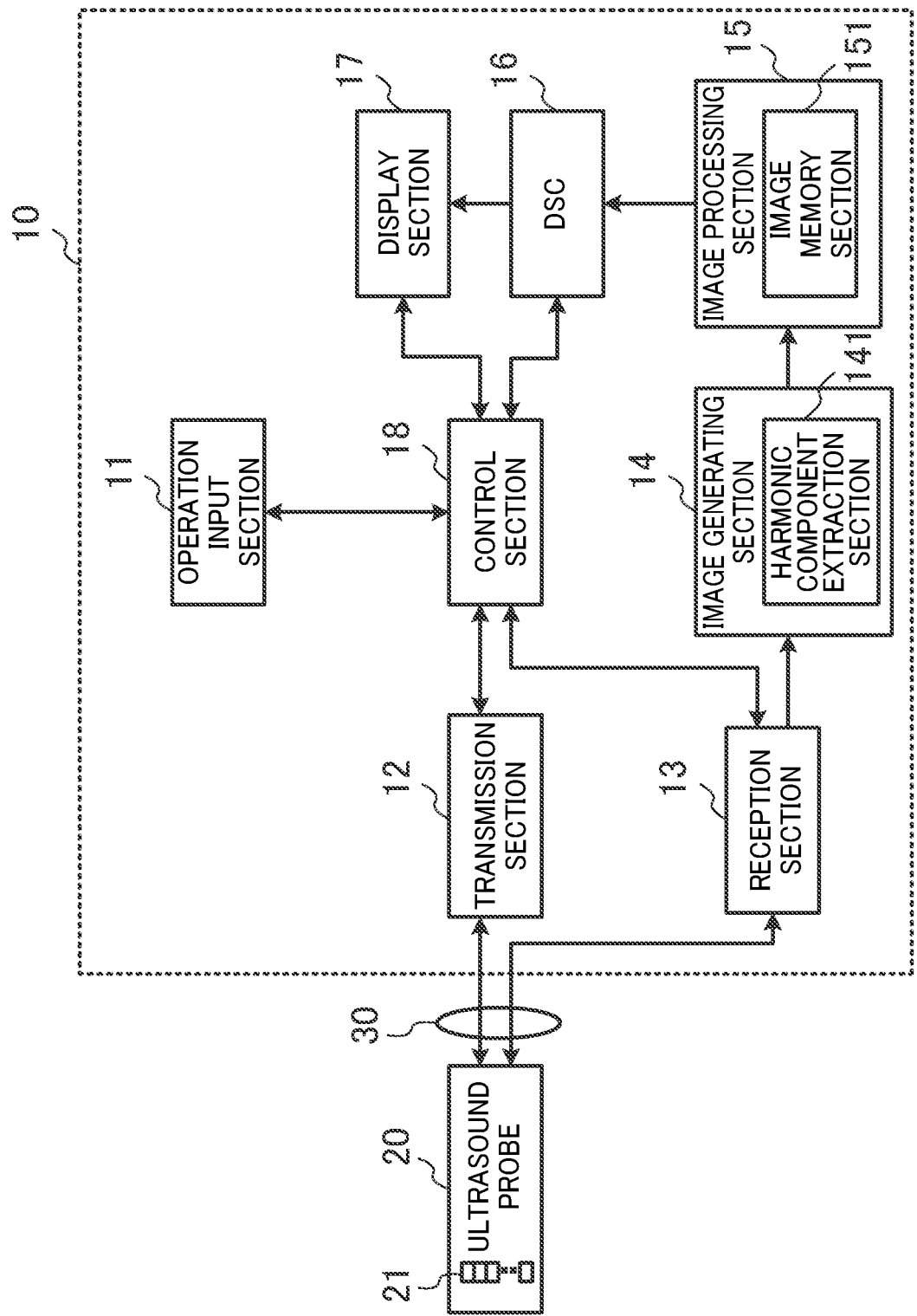
FIG. 2 is a block diagram illustrating a functional component of the ultrasound diagnostic apparatus according to the first embodiment.

As shown in FIGS. 1 and 2, ultrasound diagnostic apparatus 1 according to the first embodiment includes ultrasound diagnostic apparatus body 10 and ultrasound probe 20. FIG. 1 is a diagram illustrating an external configuration of ultrasound diagnostic apparatus 1. FIG. 2 is a block diagram illustrating a functional component of ultrasound diagnostic apparatus 1 according to the first embodiment.

Ultrasound probe 20 transmits an ultrasound wave to a subject such as a living body (not shown) and receives a reflected wave (reflected ultrasound: echo) reflected by the subject.

Ultrasound diagnostic apparatus body 10 is connected to ultrasound probe 20 via cable 30, and transmits an electrical drive signal to ultrasound probe 20, thereby transmitting a transmission ultrasound wave to the subject. Further, Ultrasound diagnostic apparatus body 10 receives an electrical reception signal generated by ultrasound probe 20 based on the reflected ultrasound from the subject received by ultrasound probe 20, and images the internal state in the subject by using the reception signal, thereby providing an ultrasound diagnostic image.

Ultrasound probe 20 includes a plurality of transducers 21. The plurality of transducers 21 are arranged in a one-dimensional array in the azimuth direction, for example. In this embodiment, ultrasound probe 20 includes, for example, several tens to several hundreds of transducers 21. Note that transducers 21 may be arranged in a two-dimensional array.

In the first embodiment, a capacitive micromachining ultrasound transducer (cMUT) elements are used as the plurality of transducers 21 included in ultrasound probe 20. A cMUT element is formed using semiconductor manufacturing technology (MEMS) and facilitates wiring to each element, and therefore has advantages such as suitability for a multidimensional array and ease of circuit integration.

However, the cMUT element has a structure in which sound waves are output when the diaphragm provided on the substrate vibrates up and down and the vibration characteristic is vertically asymmetrical, and therefore has a problem in that it transmits an asymmetrical ultrasound wave in response to an input of a symmetrical drive signal. Since the fundamental wave component cannot be sufficiently canceled from the asymmetrical transmission ultrasound wave and it is difficult to generate a clear harmonic ultrasound diagnostic image, ultrasound diagnostic apparatus 1 according to the first embodiment addresses this problem through the operation of ultrasound diagnostic apparatus body 10.

For example, as shown in FIG. 2, ultrasound diagnostic apparatus body 10 includes operation input section 11, transmission section 12, reception section 13, image generating section 14, image processing section 15, DSC 16, display section 17, and control section 18.

Operation input section 11 includes, for example, various switches, buttons, a trackball, a mouse, a keyboard, and the like for inputting data, such as a command for starting diagnosis and personal information on a subject, and outputs an operation signal to control section 18.

Transmission section 12 supplies an electrical drive signal for generating transmission ultrasound to ultrasound probe 20 via cable 30, according to the control by control section 18. For example, transmission section 12 generates a transmission ultrasound wave by outputting a drive signal to a continuous part of all the transducers arranged in ultrasound probe 20. Transmission section 12 then shifts the transducer, which outputs the drive signal, to the azimuth direction, each time a transmission ultrasound wave is generated. Hence, ultrasound diagnostic apparatus 1 can scan a wide area while moving the scanning line.

Transmission section 12 also outputs a drive signal based on the pulse inversion method to ultrasound probe 20 for tissue harmonic imaging. To be specific, transmission section 12 transmits a first drive signal and a second drive signal having a different waveform from the first drive signal to the same scanning line with a time interval. Details of transmission section 12 will be described later.

Reception section 13 is a circuit that receives an electrical reception signal from ultrasound probe 20 via cable 30 under the control by control section 18. Reception section 13 amplifies the reception signal for each transducer 21 with a predetermined amplification factor set in advance, performs analog-digital conversion (A/D conversion), and then performs phasing addition to obtain sound ray data.

Image generating section 14 performs processing, such as envelope detection processing and logarithmic amplification, on the sound ray data from reception section 13, performs gain adjustment and the like for luminance conversion, thereby generating B-mode image data. B-mode image data is image data representing the intensity of a reception signal by luminance The B-mode image data generated by image generating section 14 is transmitted to image processing section 15. Image generating section 14 includes harmonic component extraction section 141, and generates B-mode image data by using the harmonic component extracted by harmonic component extraction section 141.

Harmonic component extraction section 141 extracts a harmonic component, according to the reception signal output from reception section 13 for tissue harmonic imaging. In this embodiment, harmonic component extraction section 141 extracts signal components mainly composed of even-order harmonics represented by second-order harmonics. Even-order harmonic components are extracted by synthesizing (for example, adding) reception signals from reflected ultrasound waves respectively corresponding to two transmission ultrasound waves transmitted according to two different types of pulse signals; removing the fundamental wave component from the reception signal; and performing filtering. B-mode image data may also be generated by performing, in addition to the aforementioned operation, other reception signal synthesis (for example, subtraction) to extract other orders (for example, odd-order harmonic components represented by third-order harmonics), and synthesizing them with even-order harmonic components.

Image processing section 15 includes image memory section 151 composed of a semiconductor memory, such as a dynamic random access memory (DRAM). Image processing section 15 stores B-mode image data output from image generating section 14, in image memory section 151 in units of frames. Image data in units of frames may be referred to as ultrasound image data or frame image data. Image processing section 15 appropriately reads the ultrasound image data stored in image memory section 151 and outputs it to DSC 16.

DSC 16 converts the ultrasound image data received from image processing section 15 into an image signal based on the television signal scanning method, and outputs the image signal to display section 17.

Display section 17 may be a display apparatus such as an liquid crystal display (LCD), a cathode-ray tube (CRT) display, an organic electronic luminescent (EL) display, an inorganic EL display, or a plasma display. Display section 17 displays an ultrasound image on the display screen according to the image signal output from DSC 16.

Control section 18 includes, for example, a central processing unit (CPU), a read only memory (ROM), and a random access memory (RAM), reads various processing programs such as a system program stored in the ROM and expands it to the RAM, and centrally controls the operation of each section of ultrasound diagnostic apparatus 1 according to the expanded program.

The ROM is a nonvolatile memory composed of, for example, a semiconductor, and stores a system program related to ultrasound diagnostic apparatus 1, various processing programs that can be executed on the system program, various data, and the like. These programs are stored in the form of computer-readable program codes, and the CPU sequentially executes operations according to the program codes. The RAM forms a work area for temporarily storing various programs executed by the CPU and data related to these programs.

[Configuration of Transmission Section 12]

Figure 3:
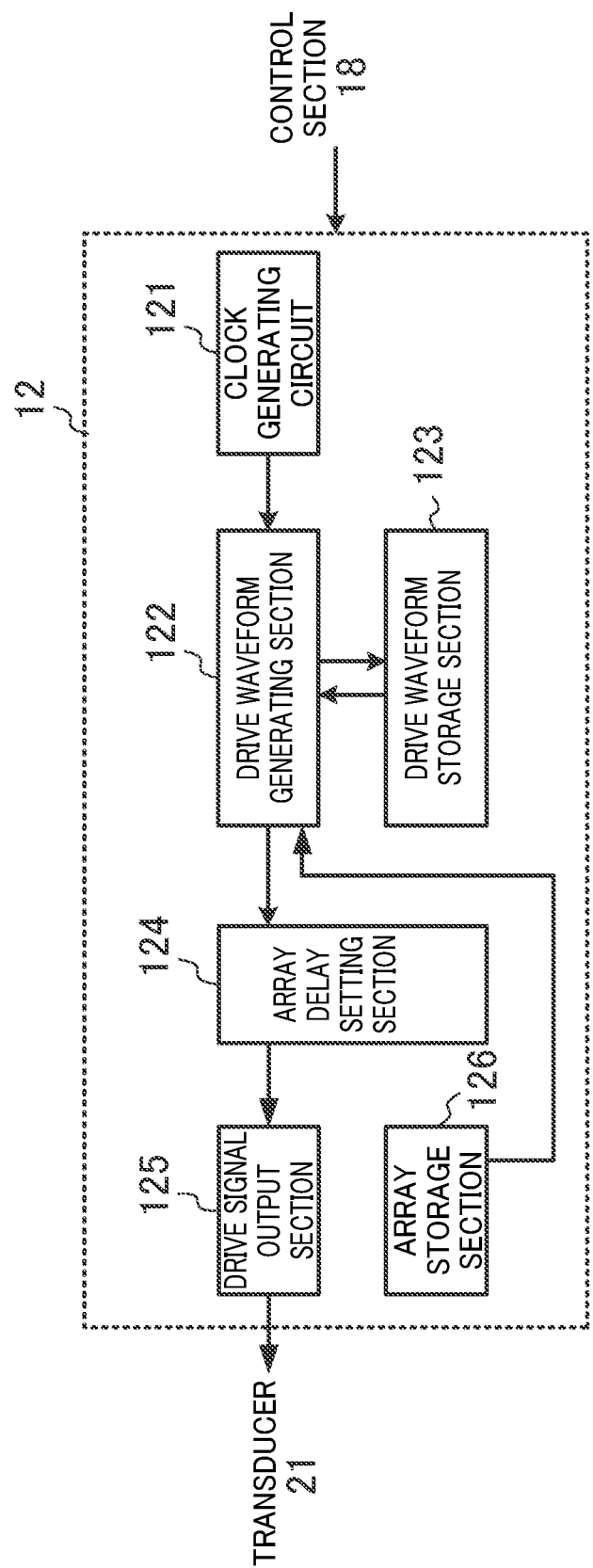
FIG. 3 is a diagram illustrating the configuration of a transmission section in the first embodiment.

The configuration and operation of transmission section 12 according to the first embodiment will be described below in detail. FIG. 3 is a diagram illustrating the configuration of transmission section 12 according to the first embodiment. As shown in FIG. 3, transmission section 12 includes clock generating circuit 121, drive waveform generating section 122, drive waveform storage section 123, array delay setting section 124, drive signal output section 125, and array storage section 126.

Clock generating circuit 121 is a circuit that generates a clock signal that determines the transmission timing and transmission frequency of the drive signal.

Drive waveform generating section 122 is a circuit for generating a drive waveform signal at a predetermined cycle. Drive waveform generating section 122 can generate a rectangular drive waveform signal by reading the drive waveform information stored in drive waveform storage section 123 and performing switching between a plurality of levels of voltage according to the waveform array information stored in array storage section 126 which will be described later. The plurality of levels of voltage are, for example, three levels of +HV, 0 (GND), and −HV, or five levels of +HV, +MV, 0 (GND), −MV, and −HV. In this specification, a case will be described in which a drive waveform generating section (in this specification, this is referred to as a three-value pulsar) that can output three levels of voltage is used as drive waveform generating section 122. Such a three-value pulsar is less expensive than, for example, a pulsar capable of arbitrarily changing the voltage steplessly, and thus is suitable for suppressing the manufacturing cost of ultrasound diagnostic apparatus 1.

Further, drive waveform generating section 122 generates a first drive waveform signal and a second drive waveform signal for the pulse inversion method, according to the control by control section 18.

In the first embodiment, the drive waveform signals generated by drive waveform generating section 122 have the same positive polarity and negative polarity. In other words, the first drive waveform signal and the second drive waveform signal generated by drive waveform generating section 122 are drive waveform signals that are positive-negative inverted from each other when the same waveform is selected.

Drive waveform storage section 123 stores a plurality of pieces of information on drive waveforms designed in advance. Drive waveform storage section 123 outputs drive waveform information responsive to a request from drive waveform generating section 122, to drive waveform generating section 122.

Array delay setting section 124 assigns a drive waveform signal to each of the plurality of transducers 21 included in ultrasound probe 20, based on the information in the array storage section, and further sets a delay time according to the transmission focal depth. Hence, the drive timing of each of the plurality of transducers 21 can be controlled.

In response to the drive control signal for each transducer 21 generated by array delay setting section 124, drive signal output section 125 outputs a drive signal responsive to a set voltage to each of the plurality of transducers 21 included in ultrasound probe 20.

Array storage section 126 stores drive signal array data. Array storage section 126 is a storage medium such as a nonvolatile memory, for example.

The drive signal array data is data indicating an array of the waveforms of drive signals output to, of the plurality of transducers 21 included in ultrasound probe 20, a predetermined number of transducers 21 adjacent to each other. FIG.

4 is a diagram showing an example of drive signal array data. FIG. 4 shows an example of array of waveforms of drive signals output to 11 transducers 21 adjacent to each other. Here, a waveform array indicates information on the selection (type) of the waveforms of drive signals output to transducers 21 adjacent to each other.

FIG. 4 shows only the array of waveforms of drive signals for the 11 adjacent transducers 21. For the other transducers 21, the array of waveforms of drive signals shown in FIG. 4 is repeatedly used. The details of the array of waveforms of drive signals output to the plurality of transducers 21 will be described later.

In FIG. 4, "1" to "11" in the upper row are numbers indicating the adjacent transducers 21, and "W1", "W1a", and "W1b" in the lower row are drive signals having different waveforms. The drive signals W1a and W1b are drive signals having waveforms for compensating for the asymmetry of transducers 21 (cMUTs).

[Method of Generating Drive Signal Array Data]

Next, a method of generating drive signal array data will be described. The drive signal array data generating processing described below is processing that is performed before ultrasound diagnostic apparatus 1 is actually used for ultrasound diagnosis. FIGS. 5A to 5F are diagrams for explaining the flow of generation of drive signal array data. Although the following drive signal array data generating processing may be performed by, for example, a computer outside ultrasound diagnostic apparatus 1 or using a part of the configuration of ultrasound diagnostic apparatus body 10 (for example, control section 18), in an ultrasound diagnostic apparatus used for a human body, it is preferable to use only a combination limited at the design level in order to ensure acoustic safety. The generated drive signal array data is stored in ultrasound diagnostic apparatus body 10 and is set as a drive condition for each transducer 21 for generating an ultrasound image.

A method of generating each drive waveform and drive signal array will be described below in detail. First, ultrasound probe 20 is used to measure the waveform (transmission sound pressure waveform) of transmission ultrasound wave output from each transducer 21 in response to an input of a drive signal. To be specific, a first drive signal for which a waveform is predetermined, and a temporary second drive signal having a waveform positive-negative inverted from the first drive signal are actually input to each transducer 21, thereby measuring the transmission sound pressure waveform output from each transducer 21. This measurement can be performed, for example, by transmitting a transmission ultrasound wave toward a hydrophone installed in water and measuring an electrical signal from the hydrophone with an external oscilloscope or the like. It is preferable that the hydrophone or oscilloscope used for the measurement be one having a sufficiently wide band with respect to the frequency band of the ultrasound wave to be transmitted.

Figure 5A:
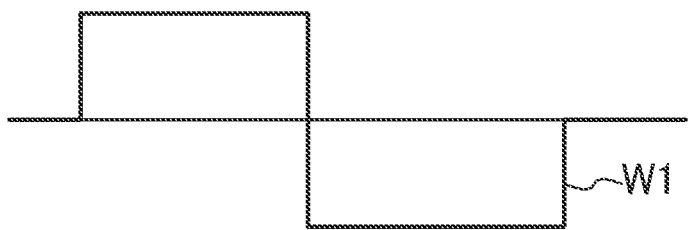
FIG. 5A is a diagram showing an example of the waveform of a first drive signal input to a transducer.
Figure 5B:
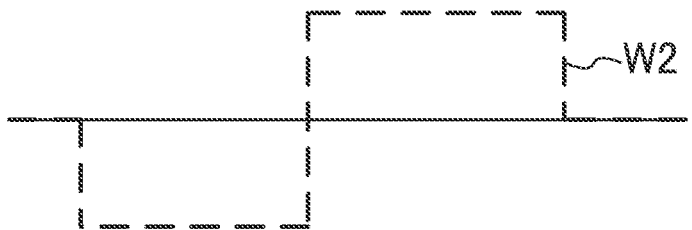
FIG. 5B is a diagram showing an example of the waveform of a second drive signal input to the transducer.
Figure 5C:
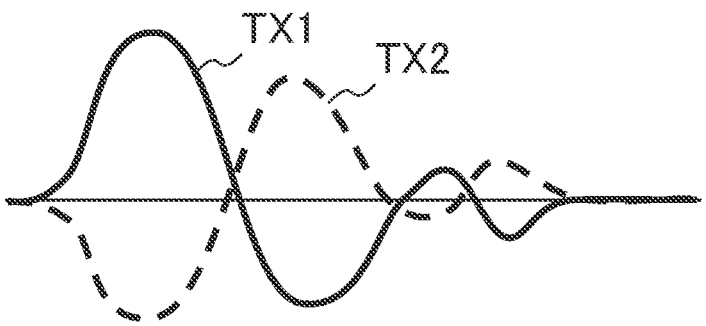
FIG. 5C is a diagram showing an example of a first transmission sound pressure waveform and a second transmission sound pressure waveform output from the transducer.

FIG. 5A is a diagram showing an example of the waveform of the first drive signal input to a transducer 21. FIG. 5B is a diagram showing an example of the waveform of the second drive signal input to the transducer 21. FIG. 5C is a diagram showing an example of the first transmission sound pressure waveform and the second transmission sound pressure waveform output from the transducer 21. As described above, in the first embodiment, cMUTs, which give an asymmetrical output response to an input, are used as transducers 21. For this reason, as shown in FIG. 5C, the inputs of the first and second drive signals are positive-negative symmetrical, whereas the transmission sound pressure waveform output from the transducer 21 is positive-negative asymmetrical. In FIGS. 5A to 5C, the waveform of the first drive signal and the waveform of the first transmission sound pressure are indicated by solid lines, and the waveform of the second drive signal and the second transmission sound pressure waveform are indicated by dotted lines. Note that the first transmission sound pressure waveform is the waveform of the transmission ultrasound wave output from the transducer 21 according to the input of the first drive signal, and the second transmission sound pressure waveform is the waveform of the transmission ultrasound wave output from the transducer 21 according to the input of the second drive signal.

In the following description, the waveform of the first drive signal is referred to as W1, and the waveform of the second drive signal is referred to as W2. For simplicity, waveform W1 of the first drive signal may be simply referred to as first drive signal W1. Similarly, waveform W2 of the second drive signal may be simply referred to as second drive signal W2.

Figure 5D:
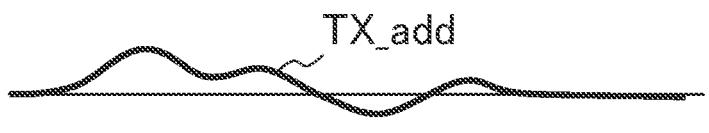
FIG. 5D is a diagram showing an example of an added transmission sound pressure waveform that is the result of adding the first transmission sound pressure waveform and the second transmission sound pressure waveform.

When first transmission sound pressure waveform TX1 and second transmission sound pressure waveform TX2 are acquired, first transmission sound pressure waveform TX1 and second transmission sound pressure waveform TX2 are added. FIG. 5D is a diagram showing an example of added transmission sound pressure waveform TX_add that is the result of addition of first transmission sound pressure waveform TX1 and second transmission sound pressure waveform TX2. As shown in FIG. 5D, due to the asymmetry of transducers 21, the addition of first transmission sound pressure waveform TX1 and second transmission sound pressure waveform TX2 is not 0.

Figure 5E:
FIG. 5E is a diagram showing an example of the waveform of a drive signal (cancellation drive waveform) for canceling the added waveform calculated using the inverse function of the transfer function of the transducer.

Next, added transmission sound pressure waveform TX_add is positive-negative inverted, and the waveform of a drive signal for cancelling added transmission sound pressure waveform TX_add using inverse function G-1(s) of transfer function G(s) of transducer 21 is generated. In this specification, the transfer function of transducer 21 refers to a function for converting the input waveform of the drive signal into a transmission sound pressure waveform that is output from transducer 21. FIG. 5E shows an example of the waveform of a drive signal (cancellation drive waveform) for cancelling the added waveform, calculated using inverse function G-1(s) of transfer function G(s) of transducer 21.

Figure 5F:
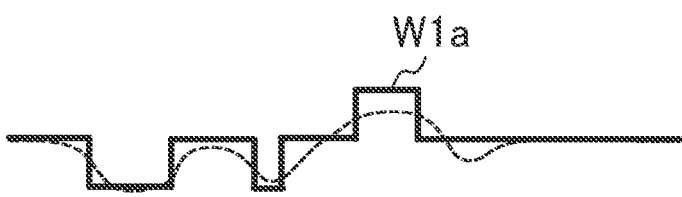
FIG. 5F is a diagram showing an example of an approximate drive waveform.

Next, approximate drive waveform W1a is generated by fitting the cancellation drive waveform shown in FIG. 5E to a three-level voltage ratio that can be taken by drive waveform generating section 122 that is a three-value pulsar. In other words, approximate drive waveform W1a illustrated in FIG. 5F is generated by setting the time that the voltage value is maintained, so as to be as close as possible to the cancellation drive waveform so as to have the same ratio as the three-level voltage value that the three-value pulsar can take. In other words, if the ratio of +HV and −HV is 1:1 as in W1 and W2, for fitting of W1a, fitting is performed under the condition that the ratio of +HV(W1a) and −HV(W1a) is 1:1. If the ratio is not 1:1, fitting is performed under the condition in which this ratio is maintained even for fitting of W1a. In other words, the ratio of +HV and −HV is the same for W1 and W1a. This makes it possible to control the difference in voltage value between W1 and W1a, which will be described later, through the ratio of waveform allocation to transducer 21. In the case where the generation of a cancellation drive waveform is repeated more than once for multiple levels such as W1a, W1b, W1c, . . . , the ratio needs to be maintained FIG. 5F is a diagram showing an example of approximate drive waveform W1a. Although fitting to three voltage values is performed because drive waveform generating section 122 is a three-value pulsar in the first embodiment, fitting to five voltage values may be performed when drive waveform generating section 122 is a five-valued pulsar which may take, for example, five voltage values. In this case, it is necessary to maintain the ratio of +HV, +MV, −MV, and −HV in the generation of a cancellation drive waveform.

Next, the amplitude ratio (|HV (W1)|:|HV (W1a)|) between waveform W1 and approximate drive waveform W1a of the first drive signal is calculated. According to this ratio, of all transducers 21 of ultrasound probe 20, the ratio of transducers 21 to which first drive signal W1 is input and transducers 21 to which approximate drive waveform W1a is input is determined. For example, when the ratio of the amplitudes of W1 and W1a is 3:1, first drive signal W1 is input to 75% of transducers 21 out of all transducers 21, and approximate drive waveform W1a is input to 25% of transducers 21. When the amplitude ratio is not an integer ratio, approximation may be made so that each value is an integer.

Subsequently, first drive signal W1 or approximate drive waveform W1a is input to each transducer 21 at the determined ratio, and first transmission sound pressure waveform TX1a transmitted by each transducer 21 is measured. Then, first transmission sound pressure waveform TX1a and second transmission sound pressure waveform TX2 are added to calculate added transmission sound pressure waveform TX_adda. Approximate drive waveform W1a is a waveform for canceling the added waveform as described above, that is, a waveform for compensating for the asymmetry between first transmission sound pressure waveform TX1 and second transmission sound pressure waveform TX2 due to the asymmetry of transducers 21. For this reason, added transmission sound pressure waveform TX_adda should be a waveform close to 0 compared to added transmission sound pressure waveform TX_add obtained when approximate drive waveform W1a is not used.

Here, whether or not the amplitude (for example, amplitude average) of added transmission sound pressure waveform TX_adda is less than a predetermined threshold is determined. If the amplitude of added transmission sound pressure waveform TX_adda is not less than a predetermined threshold, processing for calculating approximate drive waveform W1b used to cancel added transmission sound pressure waveform TX_adda is newly performed. In other words, added transmission sound pressure waveform TX_adda is inverted to perform fitting to the three values that drive waveform generating section 122 can take, and approximate drive waveform W1b is newly calculated. The aforementioned processing is repeated until the amplitude of the added transmission sound pressure waveform becomes less than a predetermined threshold. Note that the threshold is appropriately set according to the characteristics (for example, resolution priority and penetration priority) expected for the transmission frequency.

At least one approximate drive waveform for canceling the added transmission sound pressure waveform is generated in this manner. A case will be described below in which the added transmission sound pressure waveform becomes less than a predetermined threshold upon generation of approximate drive waveform W1a and approximate drive waveform W1b. Suppose that the amplitude ratio between first drive signal W1 and approximate drive waveforms W1a and W1b is W1:W1a:W1b=6:3:2.

Subsequently, which of approximate drive waveforms W1a and W1b generated as described above and waveform W1 of the first drive signal is output to each of the plurality of adjacent transducers 21 is determined. To be specific, when W1:W1a:W1b=6:3:2, an array of W1, W1a, and W1b is determined so that, of 11 (=6+3+2) adjacent transducers 21, the numbers of transducers to which W1, W1a, and W1b are output become 6, 3, and 2, respectively, and the transducers to which W1, W1a, and W1b are output are most discretely arranged. FIG. 4 shows an example of array of drive signals output to each of the 11 transducers 21 as a result of the determination made as described above. In other words, FIG. 4 shows an example of drive signal array data generated to cancel the added transmission sound pressure waveform by using approximate drive waveforms W1a and W1b.

Approximate drive waveforms W1a, W1b, . . . generated as described above are stored in advance in drive waveform storage section 123. The drive signal array data is stored in advance in array storage section 126.

[Drive Signal Output Processing by Drive Signal Output Section 125]

Processing for output of drive signals to transducers 21 through drive signal output section 125 performed using the drive signal array data generated in advance as described above and stored in array storage section 126 will now be described in detail. Drive signal output section 125 first outputs a drive signal to each transducer 21 as a first drive signal, according to an array based on the drive signal array data.

In the drive signal array data illustrated in FIG. 4, as described above, for 11 adjacent transducers 21, drive signal waveforms W1, W1a, and W1b are most discretely arrayed. Drive signal output section 125 outputs a drive signal to each of the plurality of transducers 21 included in ultrasound probe 20 through the previously determined array.

To be specific, array delay setting section 124 applies the array shown by the drive signal array data symmetrically from the center of the transmission opening formed by the plurality of transducers 21, selects the corresponding drive waveform signals, and outputs a drive control signal to which a delay time corresponding to the transmission focal depth is added, to the drive signal output section. If the number of transducers 21 is greater than the number included in the array (11 in the example shown in FIG. 4), the array is repeatedly applied.

Figure 6A:
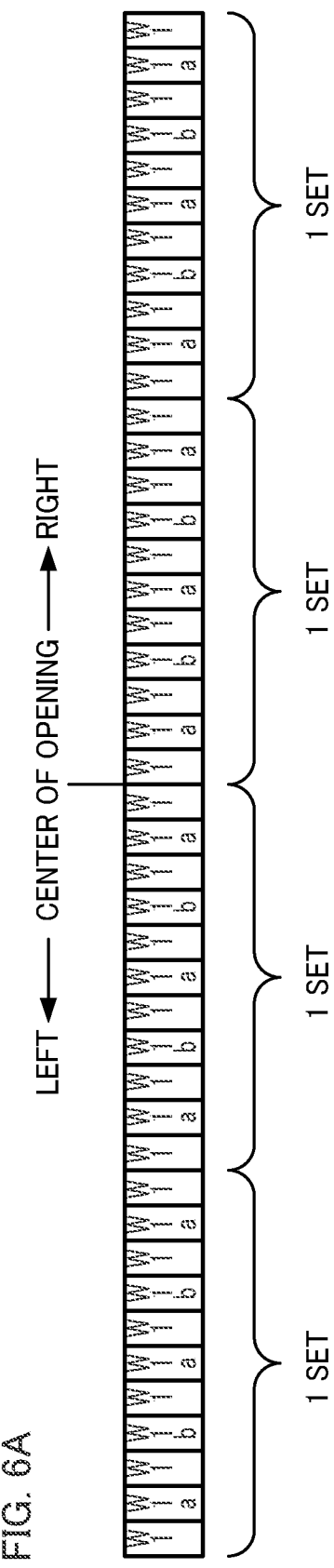
FIG. 6A is a diagram illustrating an array of drive signals output by a drive signal output section when the number of channels of the transmission opening (the number of transducers included in the transmission opening) is 44.
Figure 6B:
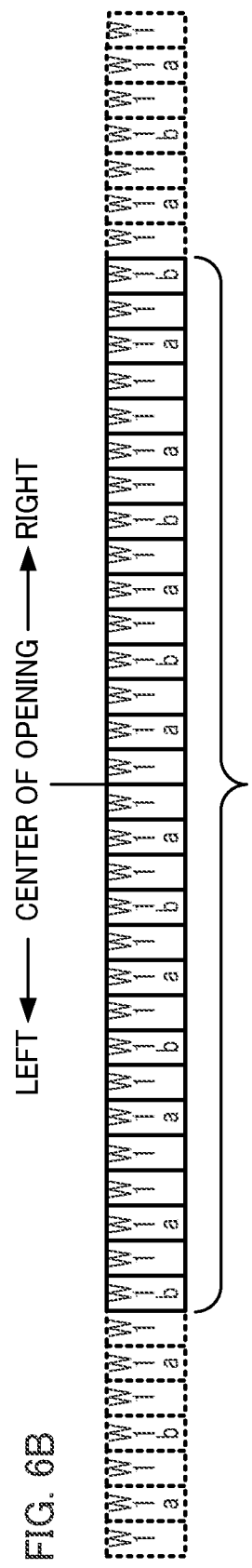
FIG. 6B is a diagram showing an array of drive signals output by the drive signal output section when the number of channels of the transmission opening is 30.
Figure 6C:
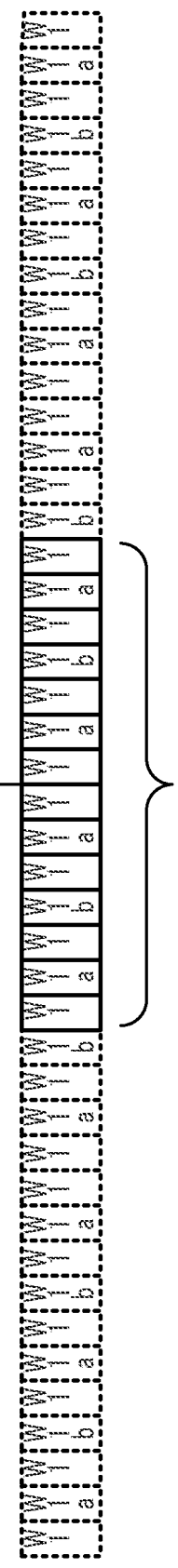
FIG. 6C is a diagram showing an array of drive signals output by the drive signal output section when the number of channels of the transmission opening is 14.

FIG. 6A is a diagram showing an array of drive signals output by drive signal output section 125 when the number of channels (the number of transducers 21 included in the transmission opening) of the transmission opening is 44. FIG. 6B is a diagram showing an array of drive signals output by drive signal output section 125 when the number of channels (the number of transducers 21 included in the transmission opening) of the transmission opening is 30. FIG. 6C is a diagram showing an array of drive signals output by drive signal output section 125 when the number of channels (the number of transducers 21 included in the transmission opening) of the transmission opening is 14.

As shown in FIG. 6A, array delay setting section 124 applies two sets of the array shown in FIG. 4 to the 22 channels on the right from the center of the transmission opening, and outputs any one of drive signals W1, W1a, and W1b. As to the right, two sets of the array shown in FIG. 4 that is made symmetrical (the array that is made symmetrical about the center of the transmission opening) are applied to the left from the center of the transmission opening. However, since the array in one set is symmetrical in FIG. 4, in the example shown in FIG. 6A, the right and the left from the transmission opening are arrayed in the same manner.

As shown in FIG. 6B, when the total number of channels of the transmission opening is 30, array delay setting section 124 extracts the 15 channels closest to the center of the transmission opening, from the channels obtained by applying an array of two sets (22 channels) on the right to the 15 channels on the right from the transmission opening. Similarly, array delay setting section 124 extracts the 15 channels closest to the center of the transmission opening, from the channels obtained by applying an array of two sets (22 channels) horizontally flipped from the array shown in FIG. 4 to the 15 channels on the left from the transmission opening.

In addition, as shown in FIG. 6C, when the total number of channels of the transmission opening is 14, array delay setting section 124 extracts the seven channels closest to the center of the transmission opening, from the channels obtained by applying an array of one set (11 channels) on the right to the seven channels on the right from the transmission opening. Similarly, array delay setting section 124 extracts the seven channels closest to the center of the transmission opening, from the channels obtained by applying an array of one set (11 channels) horizontally flipped from the array shown in FIG. 4 to the seven channels on the left from the transmission opening.

Array delay setting section 124 outputs the first drive signal to each transducer 21 as described above, and then outputs the second drive signal in a temporally shifted manner. In the first embodiment, the waveform of the second drive signal is not output with different waveforms for different transducers unlike that of the first drive signal, and the second drive signal with the same waveform is output to all transducers 21. However, the present invention is not limited to this mode: a method of arraying and transmitting a plurality of waveforms may be used for both the first and second drive signals.

In this way, drive signal output section 125 outputs drive signals having different waveforms at a predetermined ratio to a predetermined number of adjacent transducers 21, using the preset drive signal array data. Accordingly, the first transmission sound pressure waveform output from each transducer 21 in response to the input of the first drive signal, and the second transmission sound pressure waveform output from each transducer 21 in response to the input of the second drive signal are waveforms that are substantially cancelled when added. For this reason, in ultrasound diagnostic apparatus 1 according to the first embodiment, the fundamental wave in the received ultrasound wave can be suitably diminished, and a clear ultrasound image can be obtained using the harmonic component.

Second Embodiment

The second embodiment of the present invention will be described below.

[Outline of Each Component]

Figure 7:
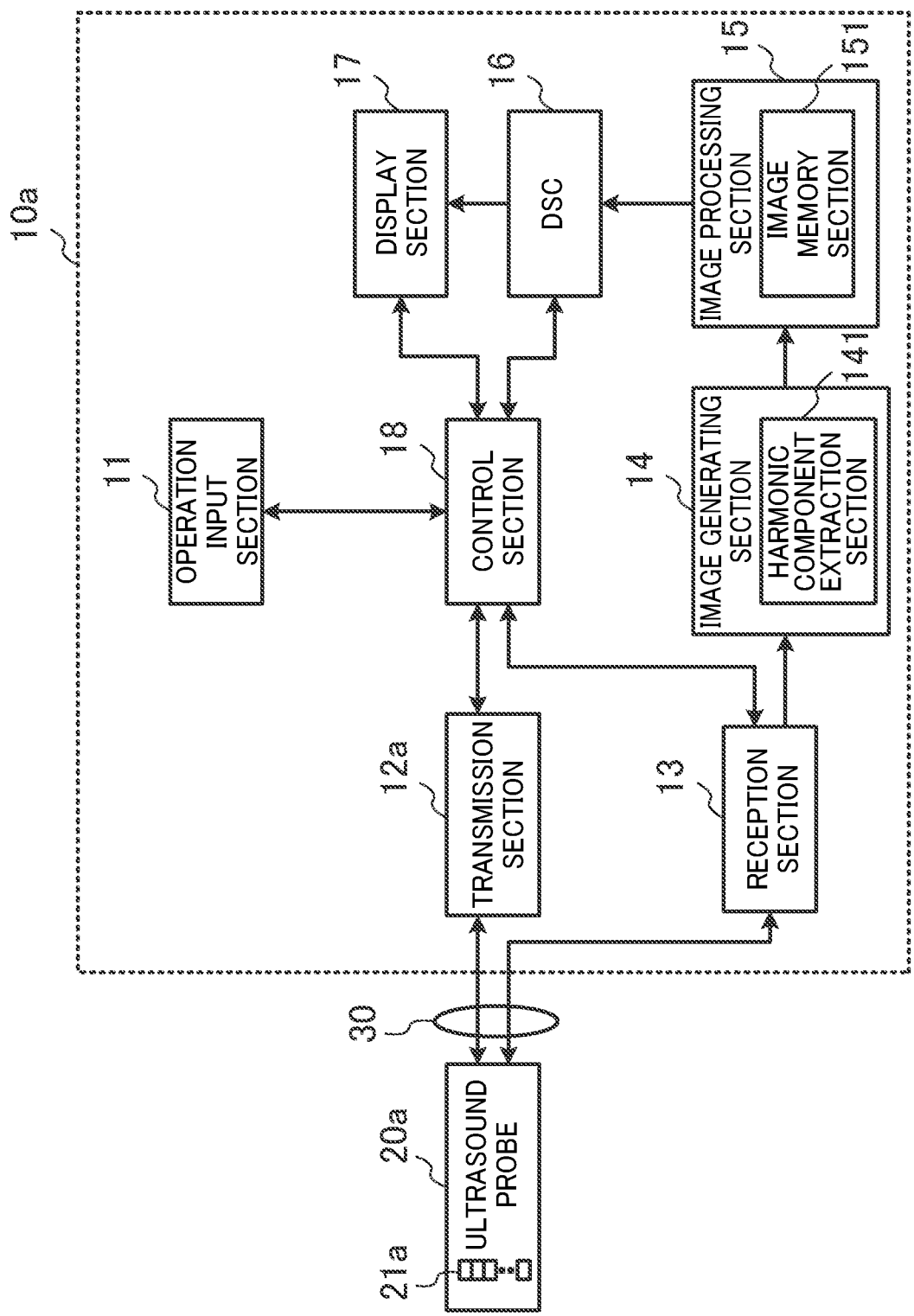
FIG. 7 is a block diagram illustrating the functional component of a ultrasound diagnostic apparatus according to the second embodiment.

FIG. 7 is a block diagram illustrating the functional component of ultrasound diagnostic apparatus 1a according to the second embodiment.

In the following description, differences between ultrasound diagnostic apparatus 1a according to the second embodiment and ultrasound diagnostic apparatus 1 according to the first embodiment described above will be mainly described, and description of similar configurations will be omitted. In FIG. 7 and FIG. 8 to be described later, the components that operate differently from those in ultrasound diagnostic apparatus 1 according to the first embodiment are denoted by reference numerals with "a".

In the second embodiment, transducers 21a of ultrasound probe 20a included in ultrasound diagnostic apparatus 1a are not cMUTs, but are transducers that output transmission sound pressure waveforms that are positive-negative symmetrical in response to the input of the positive-negative symmetrical waveform of a drive signal from, for example, a piezoelectric element. For this reason, for ultrasound diagnostic apparatus 1a according to the second embodiment, it is not necessary to consider the asymmetry of transducers 21a.

In the first embodiment, the slew rates at the rise and fall of drive waveform generating section 122 were substantially the same, that is, the time required for the rise (hereinafter referred to as rise time) and the time required for the fall (hereinafter referred to as fall time) were the same (the difference between the rise time and the fall time was almost 0). For this reason, in the first embodiment, the first drive signal and the second drive signal were signals having positive-negative symmetrical waveforms.

In order to generate a pulse signal as a drive signal for the purpose of manufacturing a compact and inexpensive ultrasound diagnostic apparatus, an inexpensive pulse generating circuit may be employed. In such an inexpensive pulse generating circuit, the slew rates at the rise and fall times may be different. The second embodiment provides ultrasound diagnostic apparatus 1a that is made considering the case where the rise time and fall time of a pulse signal (drive signal) generated by drive waveform generating section 122a are different and that can suitably diminish fundamental wave components in tissue harmonic imaging even in that case.

The second embodiment considers the case where drive waveform generating section 122a having such an asymmetry as described above outputs first drive signal DS1 and second drive signal DS2 obtained by positive-negative inverting first drive signal DS1, in a temporally shifted manner.

Figure 8A:
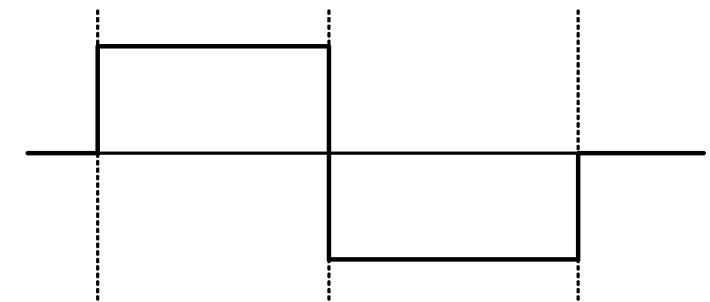
FIG. 8A is a diagram illustrating the waveform of a first pulse control signal for causing a drive waveform generating section to generate the first drive signal.
Figure 8B:
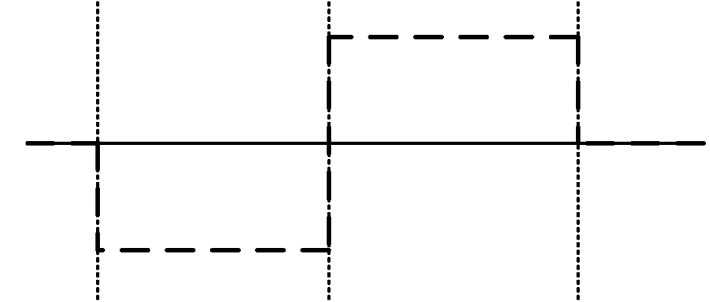
FIG. 8B is a diagram illustrating the waveform of a second pulse control signal for causing a drive waveform generating section to generate the second drive signal.
Figure 8C:
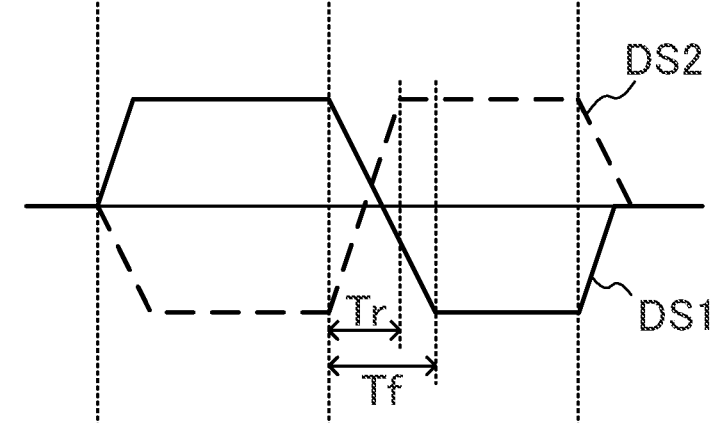
FIG. 8C is a diagram illustrating an example of pulse waveforms of the first drive signal and the second drive signal output from drive waveform generating section.

FIG. 8A is a diagram illustrating the waveform of the first pulse control signal for causing drive waveform generating section 122a to generate the first drive signal. FIG. 8B is a diagram illustrating the waveform of the second pulse control signal for causing drive waveform generating section 122a to generate the second drive signal. The details of the first pulse control signal and the second pulse control signal will be described later. FIG. 8C is a diagram illustrating an example of actual drive waveforms of first drive signal DS1 and second drive signal DS2 output from drive signal output section 125a based on the first pulse control signal and the second pulse control signal. In the example shown in FIG. 8C, it is assumed that the rise, that is, the time required for transition from −HV to +HV (rise time) is Tr, and the fall, that is, the time required for transition from +HV to −HV (fall time) is Tf, and Tr:Tf=2:3.

Figure 8D:
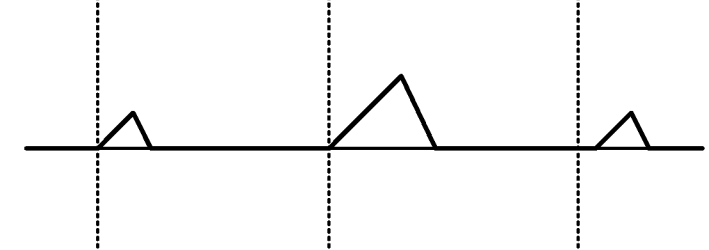
FIG. 8D is a diagram showing an added drive signal obtained by adding the first drive signal and the second drive signal shown in FIG. 8C.

FIG. 8D is a diagram showing added drive signal DS_add obtained by adding first drive signal DS1 and second drive signal DS2 shown in FIG. 8C. Since the pulse signal generated by drive signal output section 125a has a different rise time and fall time, as shown in FIG. 8D, even if first drive signal DS1 and second drive signal DS2 are added, they are not cancelled out and a difference remains. When first drive signal DS1 and second drive signal DS2 are output to transducer 21a, the waveform of the ultrasound wave (the first transmission sound pressure waveform) output from transducer 21a according to first drive signal DS1 and the waveform of the ultrasound wave (the second transmitted ultrasound wave) output from transducer 21a according to second drive signal DS2 are positive-negative asymmetrical.

For this reason, in tissue harmonic imaging using the pulse inversion method, the fundamental wave component of the received ultrasound wave cannot be canceled appropriately, which makes the extraction of harmonic components insufficient and thus makes it difficult to obtain an ultrasound image with good image quality.

Drive signal generation processing that can preferably cancel out the fundamental wave component in received ultrasound wave even with drive signal output section 125a having different rise and fall times will be described below.

Figure 9:
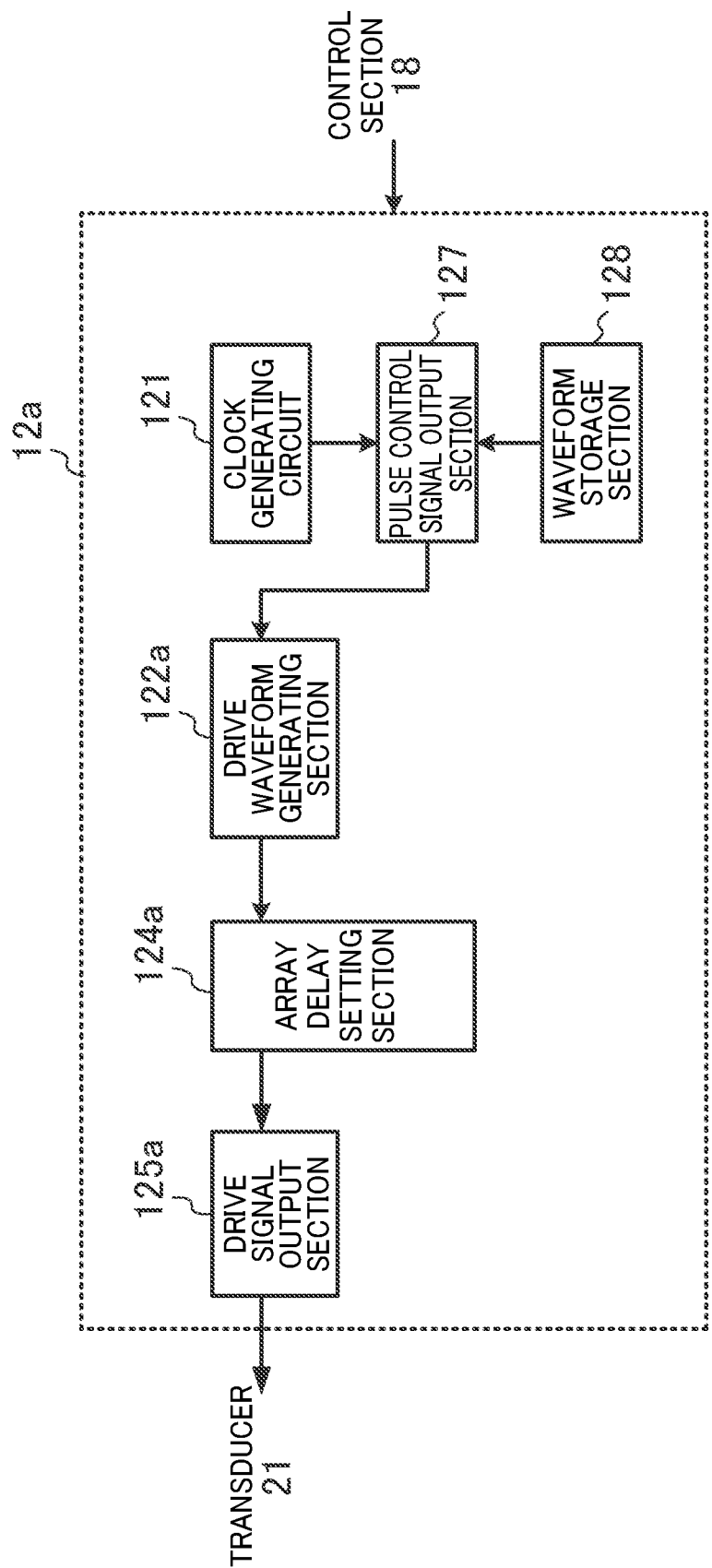
FIG. 9 is a diagram illustrating the configuration of a transmission section according to the second embodiment.

FIG. 9 is a diagram illustrating the configuration of transmission section 12a according to the second embodiment. As shown in FIG. 9, the configuration of transmission section 12a of the second embodiment is different from transmission section 12 of the first embodiment in that it does not include drive waveform storage section 123 or array storage section 126, but include pulse control signal output section 127 and waveform storage section 128.

Pulse control signal output section 127 outputs pulse control signal PS for generating a pulse signal as a drive signal at a predetermined cycle. At this time, pulse control signal output section 127 generates and outputs pulse control signal PS based on the waveform data prestored in waveform storage section 128. Waveform storage section 128 is a storage medium such as a nonvolatile memory.

Figure 10:
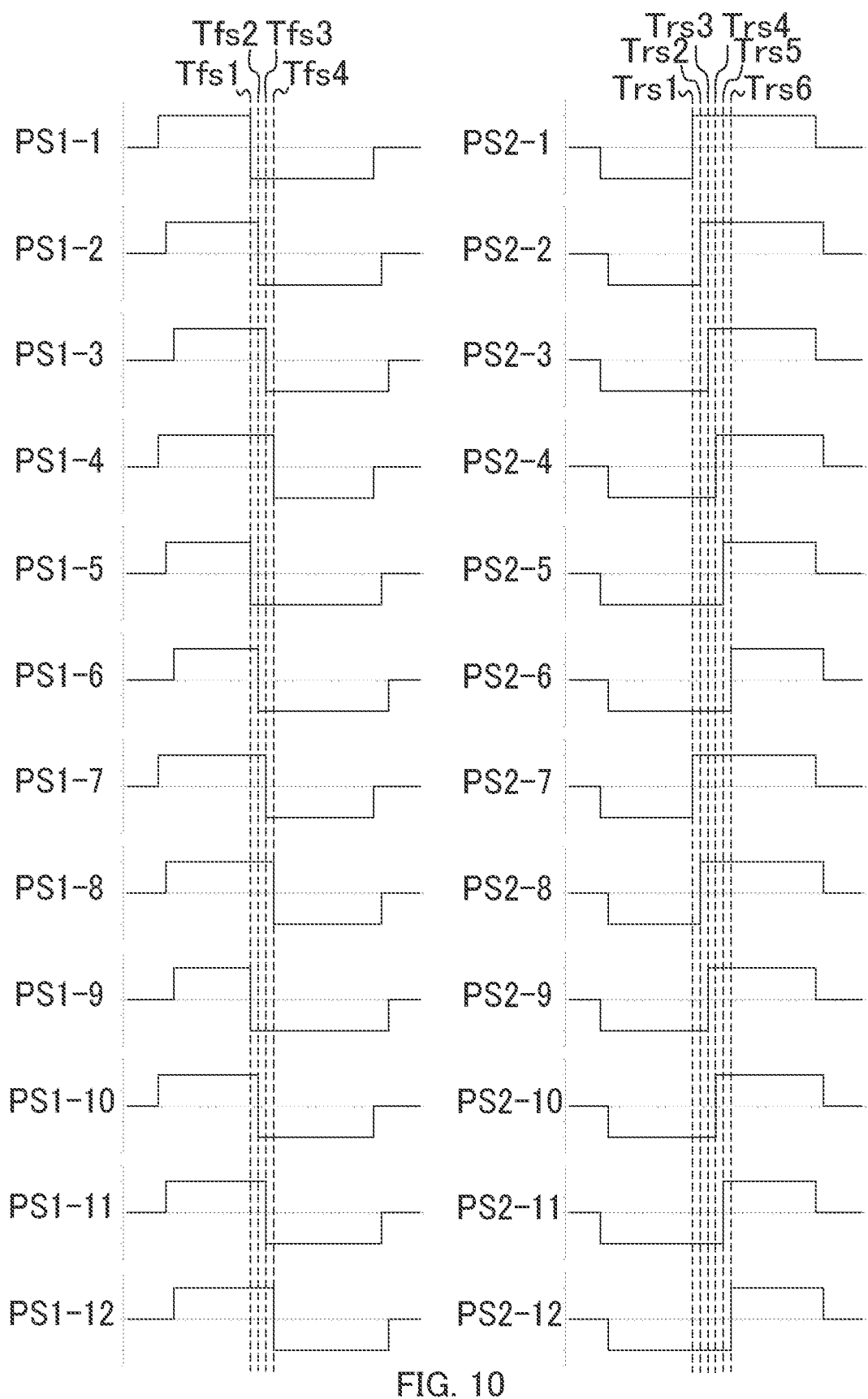
FIG. 10 is a diagram illustrating pulse control signals output from a pulse control signal output section.

FIG. 10 is a diagram illustrating pulse control signals output from pulse control signal output section 127. In FIG. 10, first pulse control signals PS1-1 to PS1-12 are control signals for outputting a first drive signal for the pulse inversion method. In addition, in FIG. 10, second pulse control signals PS2-1 to PS2-12 are control signals for outputting a second drive signal for the pulse inversion method. In the following description, first pulse control signals PS1-1 to PS1-12 and second pulse control signals PS2-1 to PS2-12 may be collectively referred to as pulse control signal PS.

As shown in FIG. 10, pulse control signal PS output from pulse control signal output section 127 has four types of fall start times (Tfs1 to Tfs4) and six types of rise start times (Trs1 to Trs6). Note that the rise start time refers to the time when the signal starts to rise, and the fall start time refers to the time when the signal starts to fall. Such a plurality of waveforms are pre-designed based on rise time Tr and fall time Tf of drive waveform generating section 122a, and are stored in waveform storage section 128 as waveform data.

As shown in FIG. 10, first pulse control signals PS1-1 to PS1-12 include signals that are asymmetrical with respect to the respective second pulse control signals PS2-1 to PS2-12. To be specific, PS1-1 and PS2-1 and PS2-7, PS1-2 and PS2-2 and PS2-8, PS1-7 and PS2-3 and PS2-9, and PS1-8 and PS2-4 and PS2-10 are signals symmetrical with respect to each other. In contrast, signals that are positive-negative symmetrical with respect to PS1-3, PS1-4, PS1-5, PS1-6, PS1-9, PS1-10, PS1-11, and PS1-12 are not included in second pulse control signals PS2-1 to PS2-12. Signals that are positive-negative symmetrical with respect to PS2-5, PS2-6, PS2-11, and PS2-12 are not included in first pulse control signals PS1-1 to PSI-12. Accordingly, first pulse control signals PS1-1 to PS1-12 can be said to be a group of positive-negative symmetrical signals that are not symmetrical at least in part with respect to second pulse control signals PS2-1 to PS2-12 regardless of how they are combined.

Pulse control signal output section 127 outputs 12 different first pulse control signals. Further, pulse control signal output section 127 outputs twelve different second pulse control signals. Note that the order of first pulse control signals PS1-1 to PS1-12 and second pulse control signals PS2-1 to PS2-12 is not limited to the example shown in FIG. 10, and they may be interchanged.

Array delay setting section 124a arrays twelve different first drive signals DS1 according to the transmission opening on the basis of twelve different first pulse control signals PS1-1 to PS1-12, and generates a drive signal to which a delay time dependent on the transmission focal depth is added. Further, array delay setting section 124a arrays twelve different second drive signals DS2 according to the transmission opening on the basis of twelve different second pulse control signals PS2-1 to PS2-12, and generates a drive signal to which a delay time dependent on the transmission focal depth is added.

Figure 11:
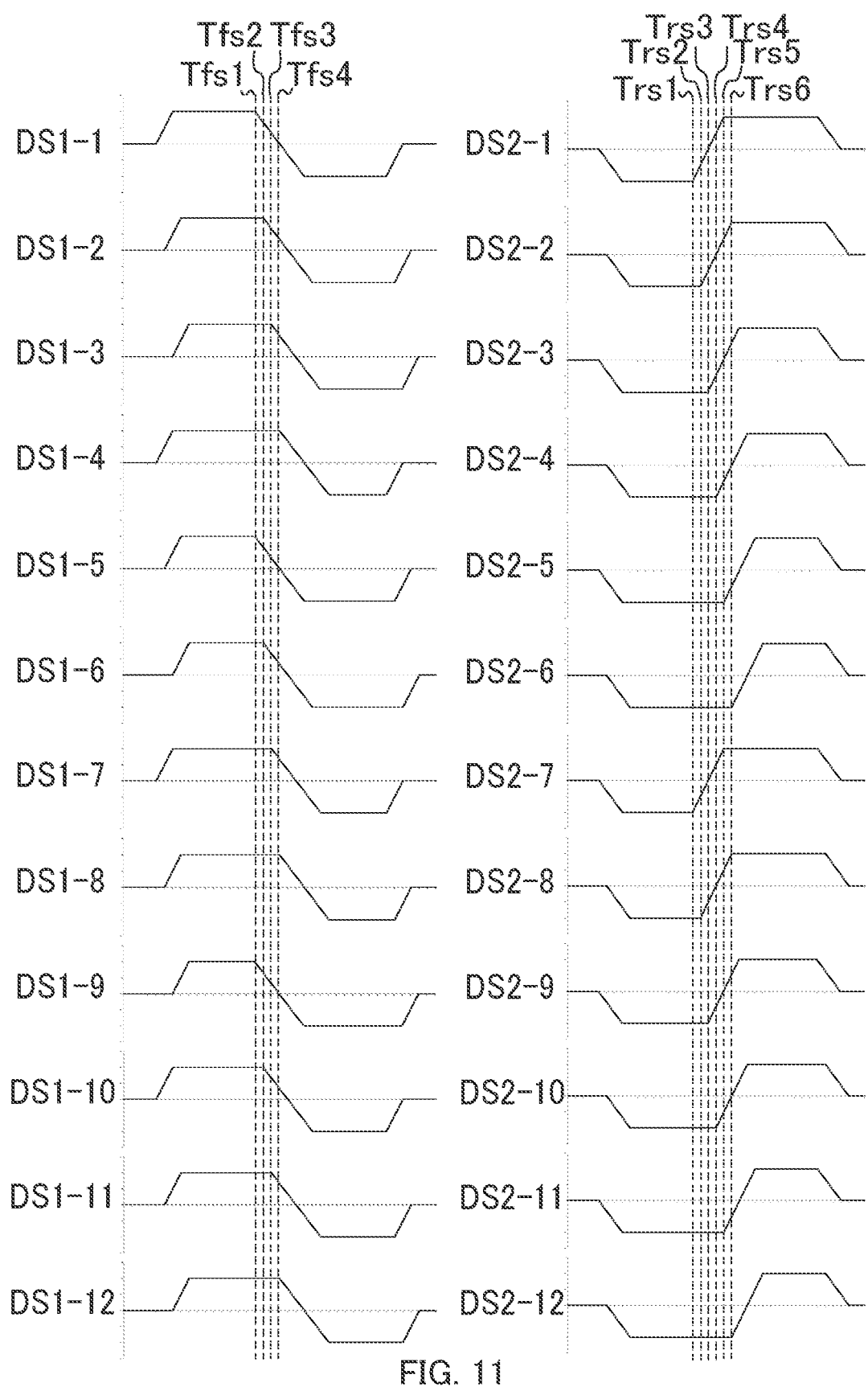
FIG. 11 is a diagram illustrating drive signals output from a pulse generating circuit.

FIG. 11 is a diagram illustrating the drive signal output from drive signal output section 125a excluding the delay time. In FIG. 11, first drive signals DS1-1 to DS1-12 are drive signals generated by drive signal output section 125a on the basis of first pulse control signals PS1-1 to PS1-12, respectively. In addition, second drive signals DS2-1 to DS2-12 are drive signals generated by drive signal output section 125a on the basis of second pulse control signals PS2-1 to PS2-12, respectively. As shown in FIG. 11, like pulse control signal PS, drive signal DS output from drive signal output section 125a has four types of fall start times (Tfs1 to Tfs4) and six types of rise start times (Tr1 to Trs6).

Further, as shown in FIG. 11, first drive signal DS1 and second drive signal DS2 generated by drive signal output section 125a based on pulse control signal PS are signals having different rise times and fall times. In the example shown in FIG. 11, the ratio of the rise time to the fall time is 2:3 as in FIG. 8A.

First drive signal DS1 and second drive signal DS2 generated by drive signal output section 125a in this manner are output to each transducer 21a. Ultrasound diagnostic apparatus 1 cancels the fundamental wave component in accordance with the ultrasound wave that is first transmission ultrasound wave output from each transducer 21a in accordance with first drive signal DS1 and reflected by a subject, and the ultrasound wave that is second transmission ultrasound wave output from each transducer 21a in accordance with second drive signal DS2 and reflected by a subject, and generates ultrasound diagnostic images by tissue harmonic imaging that extracts only the harmonic component.

At this time, in order to suitably diminish the fundamental wave component, the positive-negative symmetry between first drive signal DS1 and second drive signal DS2 is important as described above. The positive-negative symmetry between first drive signals DS1-1 to DS1-12 and second drive signals DS2-1 to DS2-12 shown in FIG. 11 will be described below.

Figure 12A:
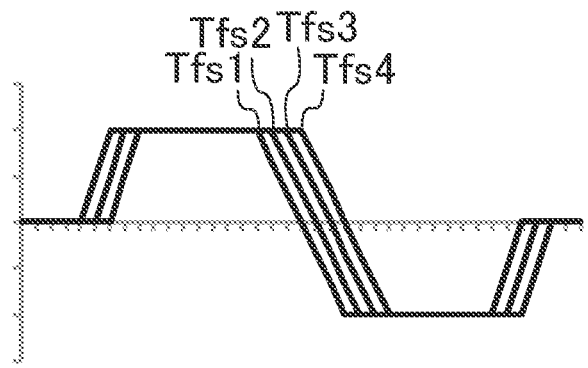
FIG. 12A is a diagram in which the first drive signal group shown in FIG. 11 are temporally overlapped.
Figure 12B:
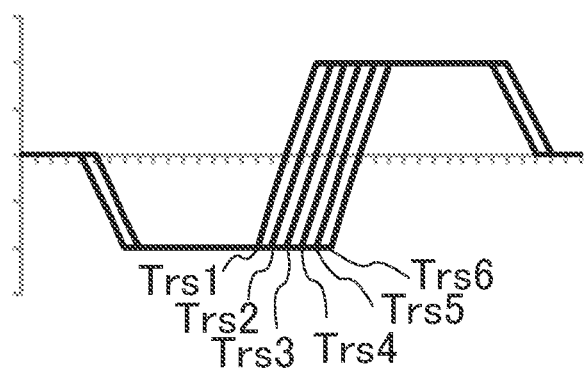
FIG. 12B is a diagram in which the second drive signal group shown in FIG. 11 are temporally overlapped.

FIG. 12A is a diagram in which first drive signals DS1-1 to DS1-12 shown in FIG. 11 are temporally overlapped. FIG. 12B is a diagram in which second drive signals DS2-1 to DS2-12 shown in FIG. 11 are temporally overlapped.

As described above and as shown in FIGS. 12A and 12B, drive signal DS generated by drive waveform generating section 122a has four types of fall start times (Tfs1 to Tfs4) and six types of rise start times (Trs1 to Trs6). The average of these drive signals DS is shown in FIG. 12C.

Figure 12C:
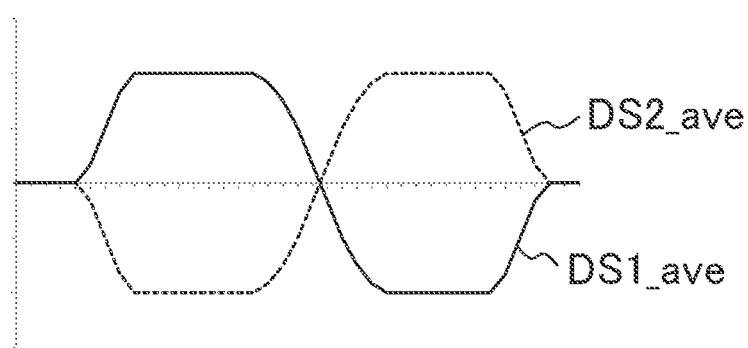
FIG. 12C is a diagram showing the average of the first drive signal group (first drive signal average) and the average of the second drive signal group (second drive signal average).

FIG. 12C is a diagram showing the average (first drive signal average) DS1_ave of first drive signals DS1-1 to DS1-12 and the average (second drive signal average) DS2_ave of second drive signals DS2-1 to DS2-12. In FIG.

12C, first drive signal average DS1_ave is indicated by a solid line, and second drive signal average DS2_ave is indicated by a dotted line.

As shown in FIG. 12C, first drive signal average DS1_ave and second drive signal average DS2_ave have waveforms that are positive-negative symmetrical with each other. Therefore, outputting first drive signals DS1-1 to DS1-12 and second drive signals DS2-1 to DS2-12 shown in FIG. 11 to transducer 21a may suitably cancel and remove a fundamental wave component in a reflected ultrasound wave. Hence, when pulse control signal output section 127 outputs a pulse control signal shown in FIG. 10 to drive waveform generating section 122a, ultrasound diagnostic apparatus 1 can provide high-quality ultrasound diagnostic images based on tissue harmonic imaging.

[Waveform Data Generating Method]

A method for generating waveform data stored in waveform storage section 128 will be described below. A plurality of waveforms included in waveform data are designed to be able to compensate for the positive-negative asymmetry between the first drive signal and the second drive signal caused by the difference between rise time Tr and fall time Tf of drive waveform generating section 122a.

Such a waveform is designed by the following method, for example. The waveform data design processing described below may be performed with, for example, a computer outside ultrasound diagnostic apparatus 1 or may be performed with a part of the configuration of ultrasound diagnostic apparatus body 10 (for example, control section 18).

First, two waveforms having the same rise time and fall time (Tr+Tf) and are positive-negative symmetrical are generated. Next, based on one of the two generated waveforms, 2 nm first waveform groups having 2n types of fall start times Tfs and the average represented by that waveform are generated, and based on the other one of the generated two waveforms, 2 nm second waveform groups having 2m types of rise start times Trs and the average represented by that waveform are generated. Note that n and m are positive integers and are numbers based on the ratio n:m between rise time Tr and fall time Tf.

In the example described above, the ratio between rise time Tr to fall time Tf is 2:3; thus, as shown in FIG. 10, 12 first drive signals DS1-1 to DS1-12 having four types of fall start time Tfs and 12 second drive signals DS2-1 to DS2-12 having six types of rise start time Trs are generated.

Such a method enables the design of waveforms for compensating for the positive-negative asymmetry between the first drive signal and the second drive signal caused by the difference between rise time Tr and fall time Tf of drive signal output section 125a.

Action and Advantageous Effects

As described above, ultrasound diagnostic apparatus 1 (1a) according to the present invention includes: transmission section 12 (12a) that generates a plurality of drive signals causing transducer 21 (21a) of ultrasound probe 20 (20a) to transmit a plurality of transmission ultrasound waves that have different waveforms in a temporally shifted manner, the drive signals being compensated for asymmetry of the transmission sound pressure waveforms of the plurality of transmission ultrasound waves transmitted from transducer 21 (21a), and outputs the drive signals to transducer 21 (21a); and image generating section 14 that acquires, from ultrasound probe 20 (20a), a reception signal based on reflected ultrasound that is the transmission ultrasound reflected in a subject, extracts a harmonic component according to a plurality of reception signals corresponding to the plurality of transmission ultrasound waves, and generates an ultrasound image based on the extracted harmonic component.

With such a configuration, also in ultrasound diagnostic apparatus 1 having a configuration in which the output response to the input signal is asymmetric, the fundamental wave component in the reception signal is suitably diminished, and a clear ultrasound diagnostic image based on the harmonic component can be generated.

Ultrasound diagnostic apparatus 1 according to the first embodiment of the present invention includes transmission section 12 that outputs, based on drive signal array data preset with which of at least one cancellation drive signal compensating for the asymmetry of the transmission sound pressure waveforms or a first drive signal being one of the plurality of drive signals is to be output to, of a plurality of transducers 21 included in ultrasound probe 20, each of a predetermined number of adjacent transducers 21, the first drive signal or the difference cancellation drive signal to each of the predetermined number of transducers 21.

With such a configuration, even when, for example, a cMUT element that outputs a plurality of transmission ultrasound waves having asymmetrical transmission sound pressure waveforms according to inputs of a plurality of symmetrical drive signals is used as the transducer 21, the fundamental wave component in the reception signal can be suitably diminished, and a clear ultrasound diagnostic image based on the harmonic component can be generated.

In ultrasound diagnostic apparatus 1a according to the second embodiment of the present invention, transmission section 12a includes: drive signal output section 125a that outputs, as the drive signal, a pulse signal having a rise time and a fall time that are different; and pulse control signal output section 127 that generates a pulse control signal for causing drive signal output section 125a to generate a plurality of drive signal groups each including a plurality of different drive signals consisting of a combination of a plurality of different rise start times and a plurality of different fall start times, and outputs the pulse control signal to drive waveform generating section 122a. The average of the drive signals included in each of a plurality of drive signal groups is 0, if addition for all drive signal groups is made.

With such a configuration, even when drive waveform generating section 122a that outputs a pulse signal having different rise time and fall time is used, the fundamental wave component in the reception signal is suitably diminished, and a clear ultrasound diagnostic image based on the harmonic component can be generated.

Although embodiments of the present invention have been described above with reference to the accompanying drawings, the present invention is not limited to these examples. It will be apparent to those skilled in the art that various changes and modifications can be made within the claims, and they are also naturally within the technical scope of the present invention. In addition, the components in the aforementioned embodiments may be arbitrarily combined without departing from the scope of the invention.

Although the aforementioned embodiments describe the case where the pulse inversion method is used to achieve tissue harmonic imaging, this is not necessarily the case in the present invention. In other words, any method other than the pulse inversion method may be used if the method can transmit the transmission ultrasound waves having different waveforms in a temporally shifted manner, and diminish the fundamental wave component in the reception signal based on these reflected ultrasound waves to suitably extract the harmonic component. To be specific, it may be applied to, for example, a method in which, based on reception signals related to ultrasound waves of three transmissions whose phases are shifted by 120°, these are combined to extract a third harmonic component.

In the first embodiment, drive signal array data is generated in advance and stored in array storage section 126, and is used to determine the drive signals to be output to a predetermined number of adjacent transducers. However, this is not necessarily the case in the present invention: the drive signal array data generating processing may be performed in real time concurrently with the ultrasound diagnostic image generating processing.

In the second embodiment, waveform data is generated in advance and stored in waveform storage section 128, and is used to determine the pulse control signal to be output to drive waveform generating section 122a. However, this is not necessarily the case in the present invention: the waveform data generating processing may be performed in real time concurrently with the ultrasound diagnostic image generating processing.

INDUSTRIAL APPLICABILITY

The present invention is suitable for an ultrasound diagnostic apparatus in which an output response to an input signal has asymmetry.

Although embodiments of the present invention have been described and illustrated in detail, the disclosed embodiments are made for purposes of illustration and example only and not limitation. The scope of the present invention should be interpreted by terms of the appended claims

What is claimed is:

1. An ultrasound diagnostic apparatus, comprising:
a transmitter that generates and outputs a plurality of drive signals to a transducer of a plurality of transducers included in an ultrasound probe, the drive signals causing the transducer to transmit a plurality of transmission ultrasound waves that have different waveforms in a temporally shifted manner, the drive signals being compensated for asymmetry of transmission sound pressure waveforms of the plurality of transmission ultrasound waves transmitted from the transducer;
a hardware processor which acquires, from the ultrasound probe, a plurality of reception signals based on reflected ultrasound waves that are the plurality of transmission ultrasound waves reflected in a subject, extracts a harmonic component from the plurality of reception signals corresponding to the plurality of transmission ultrasound waves, and generates an ultrasound image based on the extracted harmonic component; and
an array storage section that stores drive signal array data indicating a type of waveform of a drive signal to be output to each of the plurality of transducers included in the ultrasound probe,
wherein the transmitter drives each of the plurality of transducers according to the drive signal array data so that each transducer transmits the transmission ultrasound wave, and in the drive signal array data, types of the waveforms are discretely arrayed in an array direction of the plurality of transducers,
wherein the transmitter transmits causes the transducers to transmit a first ultrasound wave and a second ultrasound wave that is different from the first ultrasound wave, the hardware processor extracts a harmonic component by synthesizing a reception signal based on a first reflected ultrasound wave that is the first ultrasound wave reflected in a subject and a reception signal based on a second reflected ultrasound wave that is the second ultrasound wave reflected in a subject, and the first ultrasound wave is transmitted according to the drive signal array data,
wherein the drive signal array data includes information indicating types of waveforms of a second drive signal for transmitting the second ultrasound wave and a first drive signal having a positive-negative asymmetrical waveform, and information indicating a type of waveform that is different from the waveform of the first drive signal,
wherein the drive signal array data includes information indicating a type of waveform of a cancellation drive signal for transmitting an ultrasound wave for cancelling an ultrasound wave that is not cancelled even when an ultrasound wave transmitted according to the first drive signal and the second ultrasound wave are synthesized,
wherein the drive signal array data is arrayed in the array direction of the plurality of transducers so that the types of the waveforms are symmetrical, and the transducer outputs a plurality of transmission ultrasound waves having asymmetrical transmission sound pressure waveforms in response to inputs of a plurality of symmetrical drive signals, and
wherein the cancellation drive signal is set according to a signal generated by inverse transformation of an added sound pressure waveform based on an inverse function of a transfer function of the transducer, the added sound pressure waveform being obtained by adding the asymmetrical transmission sound pressure waveforms.

2. The ultrasound diagnostic apparatus according to claim 1, wherein the transmitter outputs at least one cancellation drive signal compensating for the asymmetry of the transmission sound pressure waveforms or a first drive signal being one of the plurality of drive signals to each of a predetermined number of adjacent transducers among the plurality of the transducers included in the ultrasound probe based on drive signal array data stored in the array storage section.

3. The ultrasound diagnostic apparatus according to claim 1, wherein the transmitter comprises:
a drive waveform generator that outputs, as the drive signal, a pulse signal having a rise time and a fall time that are different from each other; and
a pulse control signal output that generates a pulse control signal for causing the drive waveform generator to generate a plurality of drive signal groups each including a plurality of different drive signals formed of a combination of a plurality of different rise start times and a plurality of different fall start times, and outputs the pulse control signal to the drive waveform generator, wherein
the average of the waveforms of all the drive signals included in the plurality of drive signal groups is 0.

4. The ultrasound diagnostic apparatus according to claim 1, wherein a ratio between the first drive signal and the cancellation drive signal to be output to the plurality of transducers is determined according to an amplitude ratio between the first drive signal and the cancellation drive signal.

5. The ultrasound diagnostic apparatus according to claim 4, wherein in the drive signal array data, the first drive signal and the cancellation drive signal are distributed as evenly as possible among the plurality of transducers.

6. The ultrasound diagnostic apparatus according to claim 1, wherein each of the transducers is a capacitive transducer.

7. The ultrasound diagnostic apparatus according to claim 1, further comprising a waveform storage section that stores waveform data indicating waveforms of a plurality of drive signal groups to be given to each of the plurality of transducers included in the ultrasound probe, wherein
the transmitter drives each of the plurality of transducers according to the waveform data so that each transducer transmits the transmission ultrasound wave, and
the average of the waveforms of all the drive signals included in the plurality of drive signal groups indicated by the waveform data is 0.

8. The ultrasound diagnostic apparatus according to claim 7, wherein the transmitter comprises:
a pulse generating circuit that outputs a pulse signal having a rise time and a fall time that are different from each other; and
a pulse control signal output section that generates a pulse control signal for causing the pulse generating circuit to generate the plurality of drive signal groups each including a plurality of different drive signals formed of a combination of a plurality of different rise start times and a plurality of different fall start times, and outputs the pulse control signal to the pulse generating circuit.

9. The ultrasound diagnostic apparatus according to claim 8, wherein the number of the rise start times and the number of the fall start times are determined according to the ratio between the rise time and the fall time of the pulse generating circuit.

10. An ultrasound image generating method, comprising:
generating and outputting a plurality of drive signals to a transducer of a plurality of transducers included in an ultrasound probe, the drive signals causing the transducer to transmit a plurality of transmission ultrasound waves that have different waveforms in a temporally shifted manner, the drive signals being compensated for asymmetry of transmission sound pressure waveforms of the plurality of transmission ultrasound waves transmitted from the transducer;
acquiring, from the ultrasound probe, a plurality of reception signals based on a plurality of reflected ultrasound waves that are the plurality of transmission ultrasound waves reflected in a subject, extracting a harmonic component from the plurality of reception signals corresponding to the plurality of transmission ultrasound waves, and generating an ultrasound image based on the extracted harmonic component,
wherein generating the plurality of the drive signals is based on drive signal array data indicating a type of waveform of a drive signal to be output to each of the plurality of transducers included in the ultrasound probe, the drive signal array data including types of waveforms arrayed discretely in an array direction of the plurality of transducers,
wherein the transmitter transmits causes the transducers to transmit a first ultrasound wave and a second ultrasound wave that is different from the first ultrasound wave, the hardware processor extracts a harmonic component by synthesizing a reception signal based on a first reflected ultrasound wave that is the first ultrasound wave reflected in a subject and a reception signal based on a second reflected ultrasound wave that is the second ultrasound wave reflected in a subject, and the first ultrasound wave is transmitted according to the drive signal array data,
wherein the drive signal array data includes information indicating types of waveforms of a second drive signal for transmitting the second ultrasound wave and a first drive signal having a positive-negative asymmetrical waveform, and information indicating a type of waveform that is different from the waveform of the first drive signal,
wherein the drive signal array data includes information indicating a type of waveform of a cancellation drive signal for transmitting an ultrasound wave for cancelling an ultrasound wave that is not cancelled even when an ultrasound wave transmitted according to the first drive signal and the second ultrasound wave are synthesized,
wherein the drive signal array data is arrayed in the array direction of the plurality of transducers so that the types of the waveforms are symmetrical, and the transducer outputs a plurality of transmission ultrasound waves having asymmetrical transmission sound pressure waveforms in response to inputs of a plurality of symmetrical drive signals, and
wherein the cancellation drive signal is set according to a signal generated by inverse transformation of an added sound pressure waveform based on an inverse function of a transfer function of the transducer, the added sound pressure waveform being obtained by adding the asymmetrical transmission sound pressure waveforms.

11. The ultrasound image generating method according to claim 10, wherein generating the plurality of the drive signals is based on waveform data indicating waveforms of a plurality of drive signal groups to be given to each of a plurality of transducers included in an ultrasound probe, the waveform data indicating the plurality of drive signal groups where the waveforms of all the drive signals have an average of 0.

12. The ultrasound diagnostic apparatus according to claim 1, wherein the drive signals are compensated for the asymmetry of the transmission sound pressure waveforms so that an addition of transmission sound pressure waveforms of the plurality of transmission ultrasound waves is less than a predetermined threshold.

* * * * *